(12) United States Patent
Liu et al.

(10) Patent No.: US 11,479,889 B2
(45) Date of Patent: Oct. 25, 2022

(54) PROCESS FOR PRODUCING NONWOVEN AND APPARATUS SUITABLE THEREFOR

(71) Applicant: The Procter & Gamble Company, Cincinnati, OH (US)

(72) Inventors: Xiaoxin Liu, Beijing (CN); Shrish Yashwant Rane, Beijing (CN); Gerald Alain Viens, Cincinnati, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 93 days.

(21) Appl. No.: 16/422,115

(22) Filed: May 24, 2019

(65) Prior Publication Data

US 2019/0360139 A1    Nov. 28, 2019

(30) Foreign Application Priority Data

May 25, 2018    (CN) ................................. 2018088351

(51) Int. Cl.
   *D04H 3/11*    (2012.01)
   *D04H 1/492*    (2012.01)
   *D04H 18/04*    (2012.01)

(52) U.S. Cl.
   CPC ............... *D04H 3/11* (2013.01); *D04H 1/492* (2013.01); *D04H 18/04* (2013.01)

(58) Field of Classification Search
   CPC ........ D04H 18/04; D04H 1/492; D04H 1/495; D04H 1/498; D04H 1/465; D04H 3/11; D04H 5/03; D04H 1/49; D04H 18/00
   USPC .................................................. 28/104, 105
   See application file for complete search history.

(56) References Cited

U.S. PATENT DOCUMENTS

| | | | | |
|---|---|---|---|---|
| 2,862,251 A | * | 12/1958 | Kalwaites | ............. D21F 11/006 264/119 |
| 3,002,849 A | * | 10/1961 | Harmon | ................... D04H 1/68 427/194 |
| 3,033,721 A | * | 5/1962 | Kalwaites | ............. D04H 1/736 442/50 |
| 3,042,576 A | | 7/1962 | Carlyle et al. | |

(Continued)

FOREIGN PATENT DOCUMENTS

| | | |
|---|---|---|
| CN | 1149885 A | 5/1997 |
| CN | 1376224 A | 10/2002 |

(Continued)

OTHER PUBLICATIONS

All Office Actions; U.S. Appl. No. 16/422,171.

(Continued)

*Primary Examiner* — Amy Vanatta
(74) *Attorney, Agent, or Firm* — Melissa G. Krasovec (57) ABSTRACT

The present invention relates to a process and an apparatus for making a fibrous web comprising a plurality of first areas comprising hydroentangled fibers, the first areas being discrete in a machine direction and/or a counter-machine direction, wherein the process comprises subjecting a fibrous web to a first hydroentanglement process directing water jets from a water injection means comprising a plurality of orifices on to the fibrous web; blocking at least one water jet from the water injection means discontinuously by use of a first blocking member positioned between the water injection means and the fibrous web.

11 Claims, 8 Drawing Sheets

(56) References Cited

U.S. PATENT DOCUMENTS

| | | | |
|---|---|---|---|
| 3,056,406 A * | 10/1962 | Ness | D04H 1/74 604/381 |
| 3,088,859 A | 5/1963 | Harold | |
| 3,681,182 A * | 8/1972 | Kalwaites | D04H 1/736 428/131 |
| 3,750,237 A | 8/1973 | Kalwaites | |
| 4,497,095 A | 2/1985 | Minemura et al. | |
| 4,691,417 A | 9/1987 | Vuillaume | |
| 4,970,104 A | 11/1990 | Radwanski | |
| 5,670,234 A | 9/1997 | Suehr et al. | |
| 5,900,122 A * | 5/1999 | Huston | D21F 11/006 162/903 |
| 6,253,429 B1 | 7/2001 | Zolin | |
| 6,660,362 B1 * | 12/2003 | Lin | D21F 11/145 162/902 |
| 6,836,937 B1 | 1/2005 | Boscolo | |
| 7,178,210 B2 | 2/2007 | Noelle et al. | |
| 7,356,892 B2 | 4/2008 | Barth et al. | |
| 8,225,469 B2 | 7/2012 | Bevan | |
| 9,771,675 B2 | 9/2017 | Altshuler et al. | |
| 10,815,618 B2 * | 10/2020 | Brent, Jr. | D21F 11/14 |
| 2003/0134560 A1 | 7/2003 | Bevan | |
| 2004/0111847 A1 | 6/2004 | Noelle et al. | |
| 2007/0067972 A1 | 3/2007 | Muenstermann | |
| 2007/0273069 A1 | 11/2007 | Brennan et al. | |
| 2008/0120794 A1 | 5/2008 | Heller et al. | |
| 2011/0239602 A1 | 10/2011 | Furuzawa | |
| 2011/0272112 A1 | 11/2011 | Aberg et al. | |
| 2013/0101805 A1 | 4/2013 | Altshuler et al. | |
| 2015/0118403 A1 | 4/2015 | Zwick et al. | |
| 2017/0119593 A1 | 5/2017 | Hubbard, Jr. et al. | |

FOREIGN PATENT DOCUMENTS

| | | |
|---|---|---|
| CN | 1444671 A | 9/2003 |
| CN | 1451060 A | 10/2003 |
| CN | 102264971 A | 11/2011 |
| CN | 102337632 A | 2/2012 |
| CN | 103025941 A | 4/2013 |
| CN | 103249884 A | 8/2013 |
| CN | 205062378 U | 3/2016 |
| CN | 107675357 A | 2/2018 |
| EP | 0177277 A1 | 4/1986 |
| FR | 2601970 A1 | 1/1988 |
| JP | 2009/287158 A | 12/2009 |
| JP | 2011/137279 A | 7/2011 |
| WO | WO 2002/055777 A1 | 7/2002 |
| WO | WO 2012/073544 A1 | 6/2012 |
| WO | WO 2017/079599 A1 | 5/2017 |

OTHER PUBLICATIONS

PCT International Search Report, dated Feb. 25, 2019, 12 pages.
PCT International Search Report, dated Feb. 11, 2019, 10 pages.
U.S. Appl. No. 16/422,171, filed May 24, 2019, Xiaoxin Liu.
PCT Suppl. Search Report and Written Opinion for PCT/CN2018/088351 dated Aug. 21, 2020, 11 pages.

* cited by examiner

PROCESS FOR PRODUCING NONWOVEN AND APPARATUS SUITABLE THEREFOR

FIELD OF THE INVENTION

The present invention relates to a process for producing spunlace nonwoven having patterns and an apparatus suitable for the process.

BACKGROUND OF THE INVENTION

Nonwovens are widely used in a variety of personal care products including, for example feminine hygiene products such as sanitary napkins, liners and tampons, diapers and wipes since it is soft and has fabric like appearance.

Various nonwovens have been suggested for use as a component such as topsheets for absorbent articles from the standpoints of skin sensation, a feeling of dryness, comfort, absorption of expelled bodily fluids, and prevention of fluid flow-back.

It was recognized that it is also desirable in certain applications for nonwoven to be bulky. It is also desirable that nonwovens have a visible image or pattern at least one surface thereof as considered that nonwoven having images or patterns may have a breathable appearance, and delight users with a unique pattern.

In nonwovens made by conventional spunlacing, images or decorations in nonwoven material can be produced by hydroentangling. As is generally known in the art, hydroentanglement (sometimes referred to as spunlacing, jet entanglement, water entanglement, hydroentanglement or hydraulic needling), is a mechanical bonding process whereby fibers of a fibrous web are entangled by means of high pressure water jets. In hydroentanglement processes, patterning on a fibrous web can be achieved by use of a patterned support such as drums and belts which cause the fibers to form a negative image of the design on the support in the fibrous web. Conventional hydroentanglement process may not achieve clearly visible patterns in nonwoven as a sufficient difference in thickness or density between the images or decorations in a nonwoven over a background area in the nonwoven is not provided as water flow is applied to the entire surface of the nonwoven. In addition, it is costly to switch to different patterns as a support having a different image transfer surface is expensive.

WO2012/73544A discloses a nonwoven web comprising first entanglement parts and second entanglement parts which form wavy lines along a machine direction of the nonwoven web. According to WO2012/73544A, a fiber web is first hydroentangled to form an entangled web and the first parts, and the entangle web is second hydroentangled to form the second entanglement parts. In the second hydroentangling, water jets ejected from a water injector pass through perforations of a perforated member and strikes the entangled web to form the second entanglement parts. Portions of the entangled web where the water jets during the second hydroentanglement do not reach remain the first hydroentanglement parts.

It is desirable to provide a process for producing nonwoven and forming various patterns by hydroentanglement in a cost effective way.

It is also desirable to provide a process for producing nonwoven and forming various patterns by hydroentanglement without compromising bulkiness of nonwoven.

SUMMARY OF THE INVENTION

The present invention relates to a process for making a fibrous web comprising a plurality of first areas comprising hydroentangled fibers, the first areas being discrete in a machine direction. The process comprises subjecting a fibrous web to a first hydroentanglement process directing water jets from a water injection means on to the fibrous web, and blocking at least one of the water jets from the water injection means discontinuously.

The present invention also relates to an apparatus for forming a textured spunlace nonwoven web comprising a support, a water injection means in associated with the support, a first blocking member disposed between the support and the water injection means, wherein the first blocking member is movable back and forth along a first axis between a first position where the first blocking member blocks at least one water jet from the water injection means and a second position where the first blocking member does not to block the at least one water jet from the water injection means, wherein the first axis is parallel to a machine direction.

The present invention also relates to a nonwoven web having a length and a width, and comprising a plurality of first areas, and at least one second area located between two adjacent first areas in a nonwoven lengthwise direction, wherein the plurality of first areas comprise hydroentangled fibers, wherein each of the plurality of first areas comprises at least two apertures or depressions, and a land between the two apertures or depressions, and wherein the land in the first area has a higher fiber density or a higher degree of fiber entanglement than the second area.

The present invention also relates to a laminate comprising a first layer comprising a nonwoven web of the present invention.

The present invention also relates to an absorbent article comprising a layer comprising a nonwoven web or a laminate of the present invention.

BRIEF DESCRIPTION OF THE DRAWINGS

In the drawings, like numerals or other designations designate like features throughout the views.

DETAILED DESCRIPTION OF THE INVENTION

Various non-limiting forms of the present disclosure will now be described to provide an overall understanding of the principles of the structure, function, manufacture, and use of an absorbent article comprising back ears having unique engineering strain properties and low surface roughness. One or more examples of these non-limiting embodiments are illustrated in the accompanying drawings. Those ordinary skilled in the art will understand that the absorbent articles described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

"Absorbent article" refers to wearable devices, which absorb and/or contain liquid, and more specifically, refers to devices, which are placed against or in proximity to the body of the wearer to absorb and contain the various exudates discharged from the body. Absorbent articles can include diapers, training pants, adult incontinence undergarments, and feminine hygiene products such as sanitary napkins and pantyliners.

"Machine direction" or "MD" as used herein means the direction parallel to the flow of the hydroentangled fibrous web through the hydroentangled fibrous web making machine and/or absorbent article product manufacturing equipment.

"Cross machine direction" or "CD" as used herein means the direction parallel to the width of the hydroentangled fibrous web making machine and/or absorbent article product manufacturing equipment and perpendicular to the machine direction.

"Z-direction" is orthogonal to both the longitudinal and transverse directions. It is orthogonal to both the machine and cross-machine directions when the term is used with respect to a nonwoven manufacturing process.

"Disposable" is used herein to describe articles that are generally not intended to be laundered or otherwise restored or reused (i.e., they are intended to be discarded after a single use and, may be recycled, composted or otherwise disposed of in an environmentally compatible manner).

"Absorbent core" refers to a structure typically disposed between a topsheet and backsheet of an absorbent article for absorbing and containing liquid received by the absorbent article. The absorbent core may comprise one or more substrate layer, absorbent material disposed on the one or more substrate layer, and a thermoplastic adhesive composition on the absorbent material. The thermoplastic adhesive composition may be on the absorbent material and at least a portion of the one or more substrate layer. The absorbent core does not include an acquisition system, a topsheet, or a backsheet of the absorbent article. In a certain embodiment, the absorbent core would consist essentially of the one or more substrate layers, the absorbent material, the thermoplastic adhesive composition, and optionally a cover layer.

"Nonwoven" refers to a manufactured web of directionally or randomly orientated fibers, excluding paper and products which are woven, knitted, tufted, stitch-bonded incorporating binding yarns or filaments, or felted by wet-milling, whether or not additionally needled. Nonwoven materials and processes for making them are known in the art. Generally, processes for making nonwoven materials comprise laying fibers onto a forming surface, which can comprise spunlaying, meltblowing, carding, airlaying, wet-laying, coform and combinations thereof. The fibers can be of natural or man-made origin and may be staple fibers or continuous filaments or be formed in situ.

As used herein, the term "comprising" means that the various components, ingredients, or steps can be conjointly employed in practicing the present invention. Accordingly, the term "comprising" is open-ended and encompasses the more restrictive terms "consisting essentially of" and "consisting of".

Process

Figure 1:
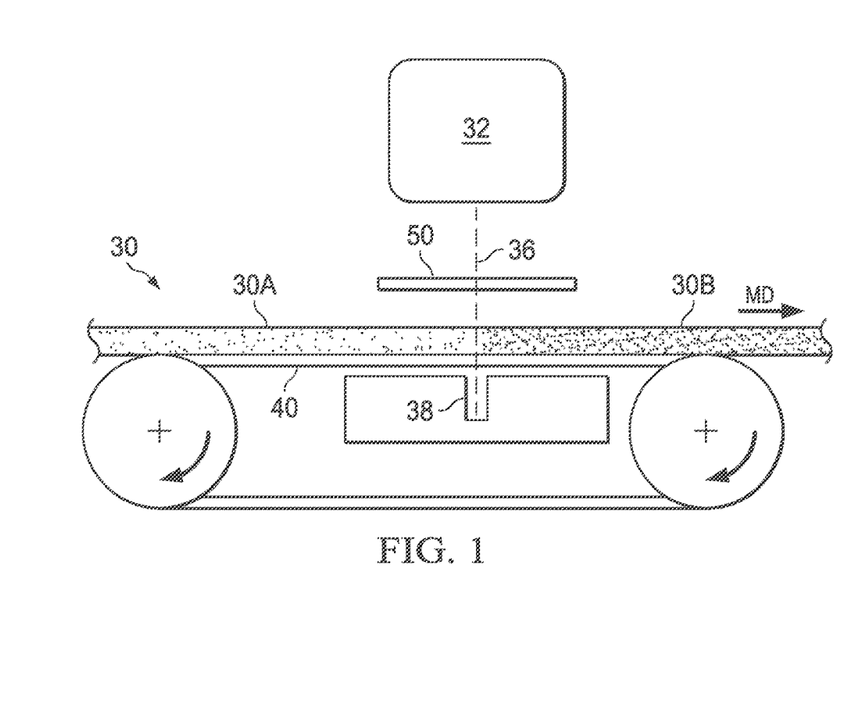
FIG. 1 is a schematic representation of a process for making a nonwoven according to the present invention.
Figure 2:
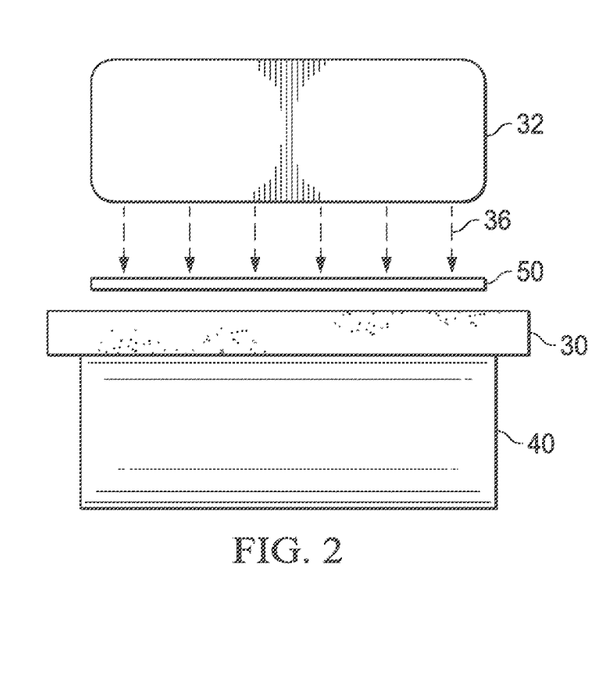
FIG. 2 is a schematic partial side view of the process in FIG. 1.

FIG. 1 depicts a simplified, schematic view of an exemplary process for making a nonwoven according to the present invention comprising a first hydroentanglement process, and FIG. 2 depicts a schematic side view of the first hydroentanglement process in the process in FIG. 1. Referring to FIGS. 1 and 2, the process according to the present invention comprises subjecting a fibrous web 30 to a first hydroentanglement process directing water jets 36 from a water injection means 32 on to the fibrous web 30, and blocking at least one of the water jets 36 from the water injection means 32 discontinuously during the first hydroentanglement process. The blocking at least one of the water jets 36 from the water injection means 32 discontinuously may be carried out by a use of a first blocking member 50 positioned between the water injection means 32 and the fibrous web 30. The first blocking member 50 comprises a non-apertured area.

Fibers forming a fibrous web can be of natural or man-made origin and may be staple fibers or continuous filaments or be formed in situ. The fibrous web which can be of various fibrous components (usually airlaid, wetlaid, or carded, but sometimes spunbond or melt-blown, etc.) can first be compacted and prewetted to eliminate air pockets prior to subjecting to a hydroentanglement process.

With reference to FIG. 1, a fibrous web 30 may have a pre-first hydroentanglement process portion 30A upstream of a first hydroentanglement process and a post-first hydroentanglement process portion 30B downstream of the first hydroentanglement process. The pre-first hydroentanglement process portion 30A may be unbonded, be bonded, or be entangled. During the first hydroentanglement process, the fibrous web 30 is passed by the water injection means 32 that comprises a plurality of orifices supplying a plurality of water jets. The plurality of orifices may be positioned to generally form a water curtain. Water jets 36 are directed through the fibrous web 30 at high pressures. The fibrous web 30 can be supported by any suitable support member 40, such as a moving wire screen or on a rotating porous drum, for example. As the water jet 36 penetrates the fibrous web 30, a suction slot 38 positioned proximate beneath the fibrous web 30 collects the water which may be filtered and returned to the water injection means 32 for subsequent injection. The water jet 36 delivered by the water injection means 32 exhausts most of its kinetic energy primarily in rearranging fibers within the fibrous web 30 to turn and twist the fibers to form a series of interlocking knots.

Still referring to FIGS. 1 and 2, in the process of the present invention, at least one of the water jets 36 from a water injection means 32 is discontinuously blocked by use of a first blocking member 50 disposed between the water injection means 32 and the fibrous web 30 (or the support member 40) by changing a location of the first blocking member 50 back and forth along a first axis, so that the nonwoven has a plurality of first areas discrete in a machine direction.

Figure 3A:
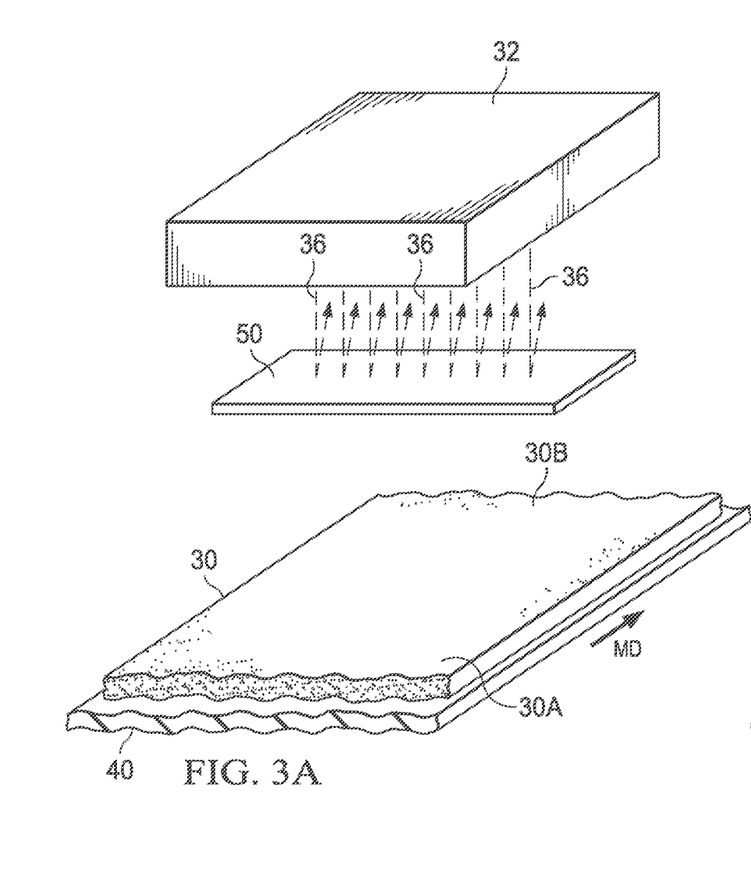
FIG. 3A is a perspective view of the process in FIG. 2.
Figure 3B:
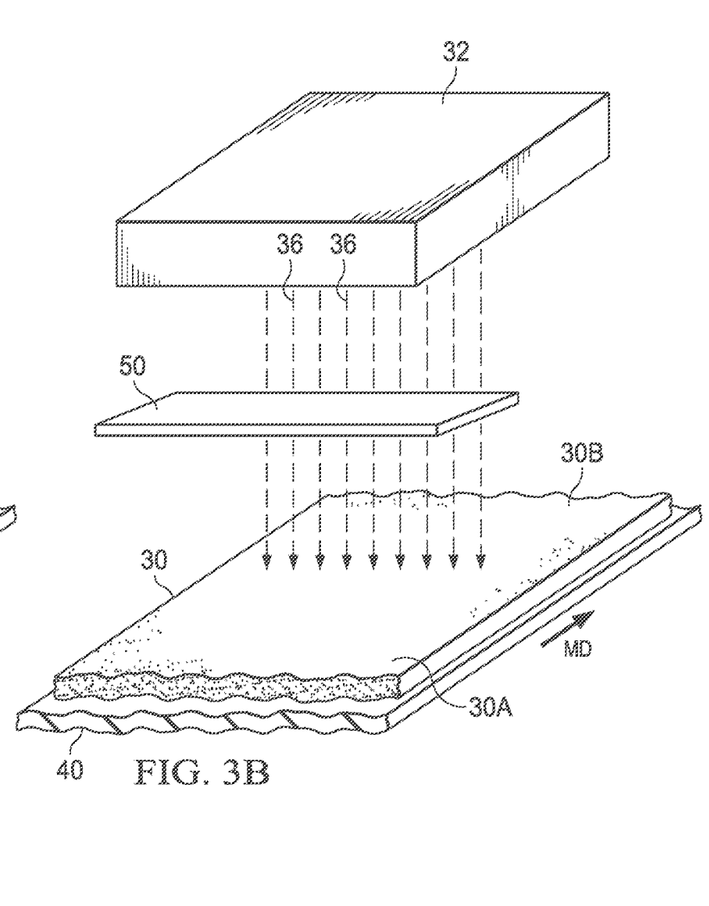
FIG. 3B is another perspective view of the process in FIG. 2.

In one embodiment, referring to FIGS. 3A and 3B, the first blocking member 50 is movable back and forth along a first axis between a first position ("blocking position") such as in FIG. 3A where the first blocking member 50 blocks at least a water jet 36 from the water injection means 32 and a second position ("open position") such as in FIG. 3B where the first blocking member 50 does not block at least one water jet 36 from the water injection means 32.

Blocking a water jet from a water injection means intends to mean that the water jet from the water injection means is blocked and is not directed to a position in a fibrous web where the water jet is supposed to hit if it is not blocked. Not-blocking a water jet from a water injection means intends to mean that the water jet from the water injection means is directed to a fibrous web along an axis in a z-direction. Referring to FIG. 3A, when the first blocking member 50 is in the first position, at least part of a non-apertured area of the first blocking member 50 is positioned between at least part of the water injection means 32 and the fibrous web 30 along an axis in a z-direction so that the first blocking member 50 blocks a water jet 36 from the water injection means 32. Referring to FIG. 3B, when the first blocking member 50 is in the second position, the water jet 36 from the water injection means 32 which is blocked by the first blocking member 50 in the first position is not blocked to be directed to on the fibrous web 30 along an axis in a z-direction. Areas in fibrous web 30 hit by the water jet(s) 36 during the first hydroentanglement process go through fiber entanglement and form a plurality of first areas discrete in the machine direction. The first blocking member 50 may maintain a first position and a second position alternately in a constant speed or in a non-constant speed. By repeating the first position and second position alternately, the plurality of first areas discrete in a machine direction are formed in the fibrous web 30. A fibrous web 30 in FIGS. 3A and 3B may have a plurality of first areas discrete in a machine direction in a post-hydroentanglement portion 30B in the fibrous web 30, though it is not reflected in FIGS. 3A and 3B only for the purpose of simplicity.

In some embodiments, a process according to the present invention comprises subjecting a fibrous web to a first hydroentanglement process directing water jets from a water injection means comprising a plurality of orifices on to the fibrous web, blocking at least one water jet from the water injection means discontinuously by use of a first blocking member positioned between the water injection means and the fibrous web, and blocking the at least one water jet from the water injection means discontinuously while the at least one water jet from the water injection means is not blocked by the first blocking member. The blocking the at least one water jet from the water injection means may be conducted by use of a second blocking member comprising at least one aperture.

The second blocking member is movable back and forth along a second axis between a third position or a blocking position where the second blocking member blocks the at least one water jet from the water injection means and a fourth position or an open position where the second blocking member does not block the at least one water jet from the water injection means. The second blocking member may be positioned between the water injection means and the first blocking member. The second blocking member may be positioned between the first blocking member and the fibrous web (or a support). The second axis may be parallel to the first axis along which the first blocking member moves back and forth. The second axis may not be parallel to the first axis. The second blocking member may maintain the third position and fourth position, for example while the at least one water jet from the water injection means is not blocked by the first blocking member, alternately. The second blocking member may maintain the third position and fourth position alternately in a constant speed or in a non-constant speed.

Figure 5A:
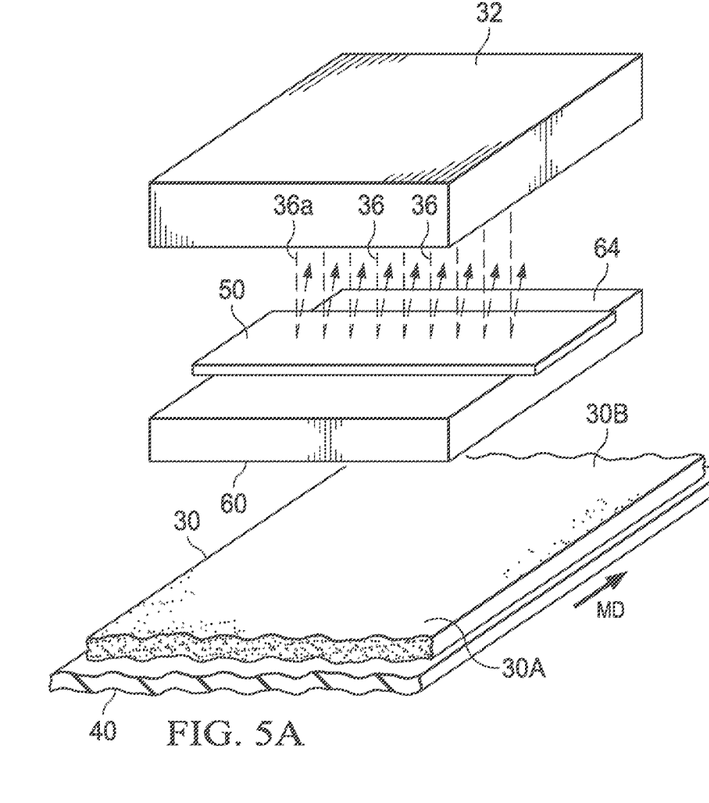
FIG. 5A is a schematic partial perspective view of another exemplary process according to the present invention.
Figure 5B:
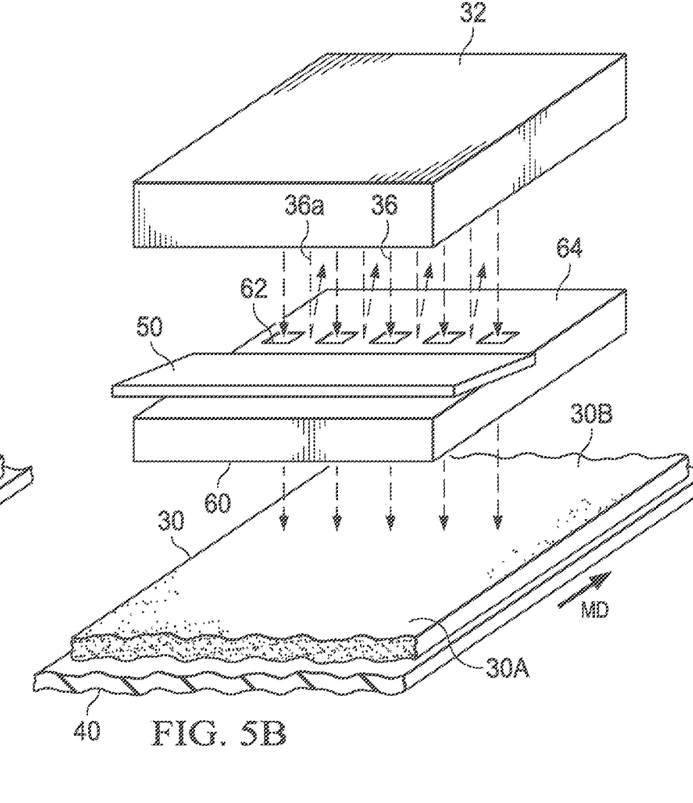
FIG. 5B is another partial perspective view of the process in FIG. 5A.
Figure 5C:
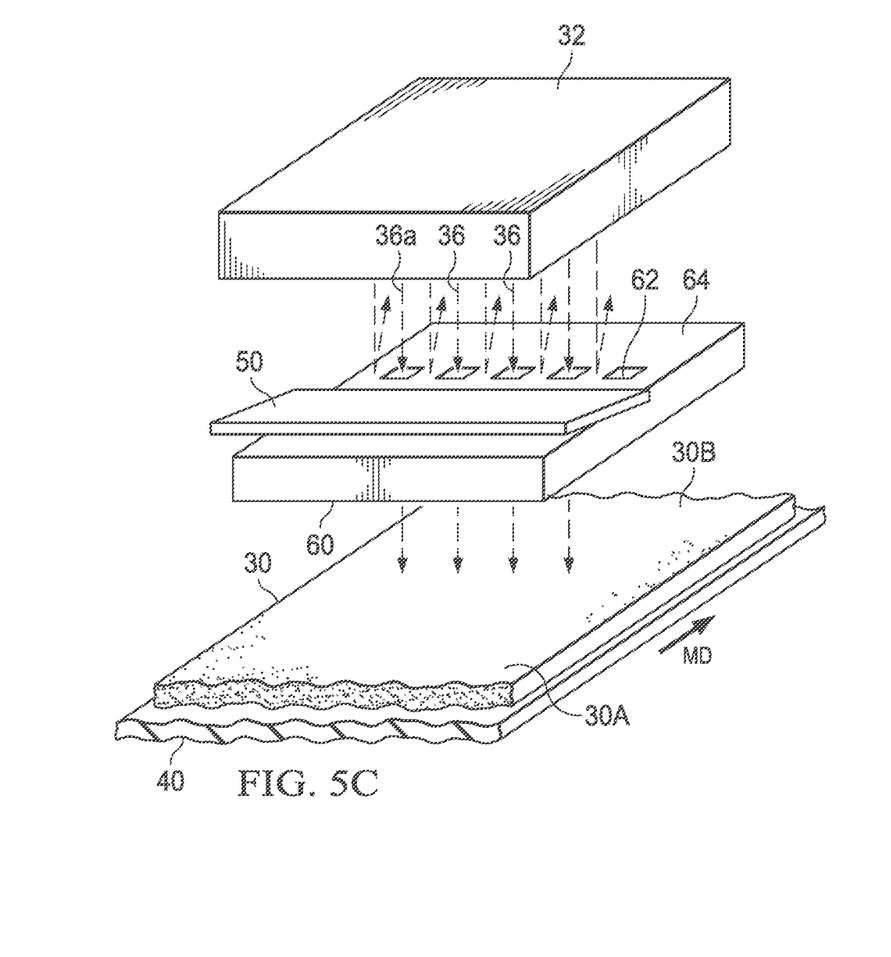
FIG. 5C is another partial perspective view of the process in FIG. 5A.

In some embodiments, referring to FIGS. 5A-5C, the first blocking member 50 moves back and forth along a first axis, in a machine direction in this case, between a first position, a blocking position, where the first blocking member 50 blocks at least one water jet 36*a* from a water injection means 32 as shown in FIG. 5A, and a second position, an open position, where the first blocking member 50 does not block the at least one water jet 36*a* from the water injection means 32 as shown in FIGS. 5B and 5C. Referring to FIGS. 5B and 5C, the second blocking member 60 comprising at least one aperture 62 and a non-apertured area 64 moves back and forth along a second axis, in a cross-machine direction for example, between a third position, a blocking position, where the second blocking member 60 blocks the at least one water jet 36*a* from the water injection means 32 as shown in FIG. 5B, and a fourth position, an open position, where the second blocking member 60 does not block the at least one water jet 36*a* from the water injection means 32 as shown in FIG. 5C. Each of the first blocking member 50 and the second blocking member 60 may be in its blocking position and open position regardless of the other blocking member's position. Referring to FIG. 5A, when the first blocking member 50 is in a first position, it blocks at least one water jet 36*a* from the water injection means 32. The second blocking member 60 may move between the third and fourth positions while the first blocking member 50 is in a first position, and the second blocking member 60 cannot pass the at least one water jet 36*a* through in both the third and fourth positions as the water jet 36*a* is blocked by the first blocking member 50. Referring to FIG. 5B, when the second blocking member 60 is in a third position (blocking position) while the first blocking member 50 is an open position, the water jet 36*a* from the water injection means 32 hits the non-aperture area 64 and does not pass through the second blocking member 60. Referring to FIG. 5C, when the second blocking member 60 is in a fourth position (open position) while the first blocking member 50 is an open position, the at least one water jet 36*a* from the water injection means 32 passes through the second blocking member 60 through an aperture 62 and is directed to on the fibrous web 30. Though FIGS. 5B and 5C indicate one water jet passes through an aperture 62 of the second blocking member 60, numbers of water jets passing through one aperture 62 in the second blocking member 60 at a given moment can be adjusted considering a design of aperture shape and size.

Areas in fibrous web 30 hit by the water jet 36, 36*a* go through fiber entanglement during the hydroentanglement process and form the plurality of first areas discrete in the machine direction. With moving back and forth the first blocking member and the optional second blocking member during hydroentanglement process, various patterns of the plurality of first areas discrete in a machine direction can be formed. Patterning can be achieved by discontinuous hydroentanglement on a fibrous web by the process of the present invention. A fibrous web 30 in FIGS. 3A and 3B, and FIGS. 5A-5C has a plurality of first areas discrete in a machine direction in a post-first hydroentanglement process portion 30B, though it is not reflected in the drawings only for the purpose of simplicity.

The first axis along which the first blocking member moves and the second axis along which the second blocking member moves may be appropriately selected as a machine direction, a cross machine direction, an oblique direction, and the like. Here, the oblique direction refers to a direction along the plane of the nonwoven fabric, or a direction in a range of more than 0 degrees and less than 90 degrees with respect to the machine direction or cross machine direction. In consideration of the ease of manufacture, the axes of the first and/or second blocking members vibration is preferably in the direction of the machine direction or cross machine direction, or a direction wherein the angle between the direction and the machine direction or cross machine direction is in the range of 0 degree to 45 degrees. In addition, the phrase "move back and forth" or "back and forth" refers to the case where the blocking member is reciprocated in a certain direction, including the case where it is reciprocated in a straight line, and the case where it is reciprocated along a circular orbit having a long axis in a certain direction. In addition, the moving direction of the first and/or second blocking members may be parallel to or not parallel to the lengthwise direction of the blocking member, and the angle between the lengthwise direction of the blocking member and the moving direction may also be changed during a process. In the process of the present invention, the blocking positions (the first and/or third position) and/or the open positions (the second and/or fourth position) may remain in the same positions during the process, or may change during the process of the present invention as long as a blocking member blocks at least one water jet from a water injection means at a blocking position and the blocking member does not block the at least one water jet from a water injection means at an open position. A moving speed of the first blocking member or the optional second blocking member may be the same. The first blocking member and the second blocking member may move in different speeds.

Hydroentangling conditions may be appropriately set depending on the weight per unit area of the web, and/or the speed of the transport support when the support member comprises a belt. For example, a water injection means with orifices having a pore size of about 0.05 to about 0.5 mm at an interval of about 0.2 to about 1.5 mm may be used, and water flow having a water pressure of about 1 to about 20 MPa may be sprayed about 1 to about 4 times to the front side and the back side of the web, respectively. More preferably, the water pressure is about 1 to about 10 MPa. When the water pressure is less than 1 MPa, the entangling between the fibers may become insufficient, and the resulting nonwoven web may be liable to fluff shedding. When the water pressure exceeds 20 MPa, the entangling among the fibers may become too strong, the degree of freedom of the fibers may be reduced, the nonwoven web may feel hardened, or the texture of the nonwoven web may be deteriorated.

Once the fibrous web has been hydroentangled, the hydroentangled fibrous web is dried for example, by being passed through a dewatering device where excess water is removed. The hydroentangled fibrous web after being dried, may be further treated with additional heat especially when the fibrous web includes synthetic fibers. The synthetic fibers begin to soften, and these softened fibers touch each other, bonds will form between the fibers, thereby increasing the overall flexural rigidity of the structure due to the formation of these bond sites. The elevated temperature of the hydroentangled fibrous web is not high enough, however, to cause other types of fibers within the hydroentangled fibrous web to flow or otherwise soften, bond, or collapse. The formation of the bond sites within the hydroentangled fibrous web adds stiffness to the web, yet the fluid handling performance of the hydroentangled fibrous web remains as desired. It will be recognized that raising the final drying stage temperature (or otherwise introducing heat to the hydroentangled fibrous web) to just above a softening temperature of a portion of the bicomponent fiber provides an increase in mechanical performance while also maintaining liquid handling performance. If, however, the hydroentangled fibrous web is heated to too high of temperature, the rigidity of the structure increases and the liquid handling performance of the structure can suffer.

Figure 4:
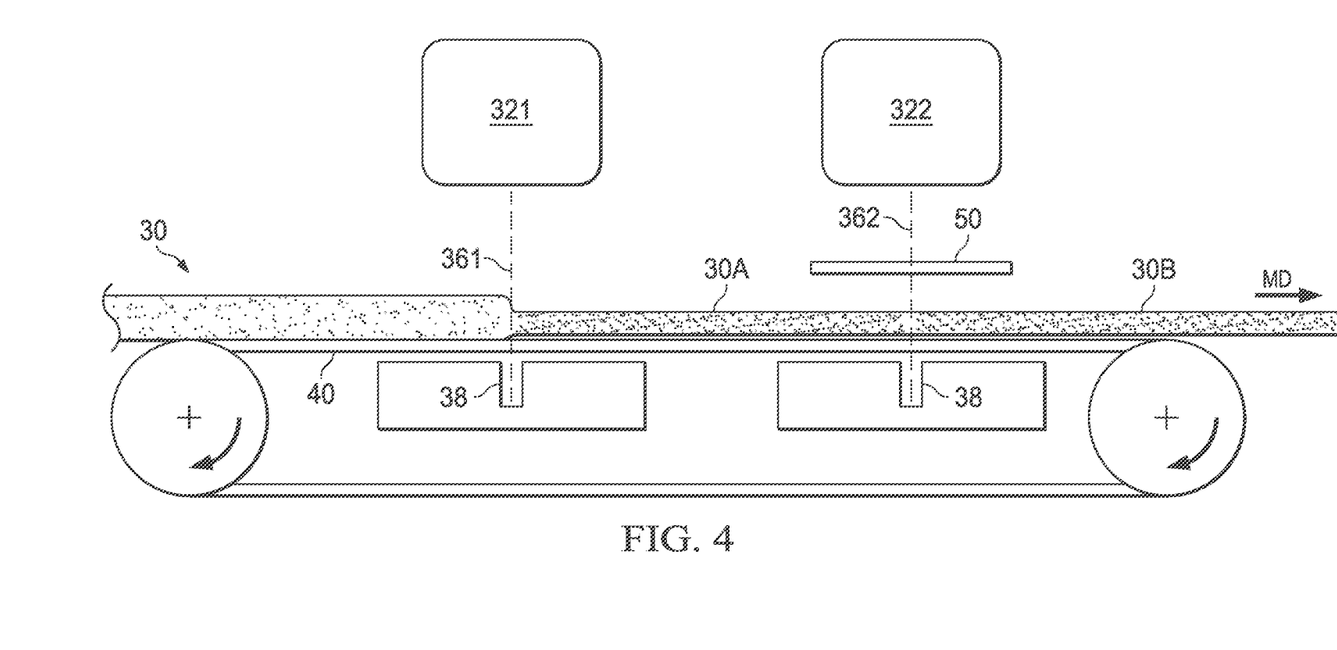
FIG. 4 is a schematic representation of another process for making a nonwoven according to the present invention.

The process of the present invention may further comprise at least one additional entanglement process such as a hydroentanglement prior to or after the first hydroentanglement process. In one embodiment, referring to FIG. 4, the process of the present invention may further comprise an additional hydroentanglement process using a water injection means 321 supplying waterjets 361 before the first hydroentanglement process using a water injection means 322 supplying water jets 362. Water jets 361 from water injection means 321 and water jets 362 from water injection means 322 may or may not be at the same pressure. The particular number of water injection means utilized for the process of the present invention can be determined based on, for example, desired basis weight, degree of bonding required, characteristics of the web, and so forth.

In some embodiments, a process according to the present invention may further comprise subjecting the fibrous web to a second hydroentanglement process. As one example of such embodiments, a process according to the present invention comprises subjecting a fibrous web to a first hydroentanglement process directing water jets from a first water injection means on to the fibrous web, blocking at least one water jet from the first water injection means discontinuously during the first hydroentanglement process, subjecting the fibrous web to a second hydroentanglement process directing water jets from a second water injection means on to the fibrous web, and blocking at least one water jet from the second water injection means discontinuously during the second hydroentanglement process.

The blocking at least one water jet from the second water injection means may be conducted by use of a third blocking member. The third blocking member in the second hydroentanglement process may be similar to the first or the optional second blocking member described herein in terms of blocking member shape and structure. The third blocking member is positioned between the second water injection means and the fibrous web, and rotates or moves between a blocking position where the third blocking member blocks at least one water jet from the second water injection and an open position where the third blocking member does not block the at least one water jet from the second water injection.

A process according to the present invention can provide nonwoven having a plurality of first areas comprising hydroentangled fibers discrete in a machine direction and at least one second area located between two adjacent first areas in the machine direction. Each of the plurality of first areas may comprise at least two apertures or depressions, and a land between the two apertures or depressions. The land in the first area and may have a higher fiber density or a higher degree of fiber entanglement than the second area.

With the second hydroentanglement process, a process according to the present invention can provide nonwoven having a plurality of first areas and at least one second area described herein, and a plurality of third areas comprising hydroentangled fibers discrete in a machine direction or in a cross-machine direction. Each of the plurality of third areas may comprise at least two apertures or depressions, and a land between the two apertures or depressions. The land in the first area and the land in the third area may have a higher fiber density or a higher degree of fiber entanglement than the second area.

Apparatus

An apparatus useful for the process of the present invention, referring to FIGS. 3A and 3B comprises a support member 40, a water injection means 32 in associated with the support member 40, and a first blocking member 50 disposed between the support member 40 and the water injection means 32.

The water injection means 32 may comprises a plurality of orifices. The plurality of orifices may be positioned to generally form a water curtain. The plurality of orifices may comprise orifices arranged at a fixed or variable interval. The plurality of orifices may comprise a plurality of orifice groups each of which comprises two or more orifices. A width of one orifice group and/or a space between adjacent orifice groups may be determined depending on patterns to be formed on the fibrous web 30. When the number of orifices included in one orifice group is 2 or more, the interval between adjacent orifices in one orifice group may be smaller than the space between the orifice group and an adjacent orifice group.

The first blocking member 50 is movable back and forth along a first axis between a first position or a blocking position where the first blocking member 50 blocks at least one water jet 36 from the water injection means 32 and a second position or an open position where the first blocking member 50 does not block the at least one water jet 36 from the water injection means 32. The first blocking member 50 may comprises at least one aperture.

In some embodiments, the apparatus according to the present invention further comprise a second blocking member which comprises at least one aperture and a non-apertured area, and is movable back and forth along a second axis between a third position or a blocking position where the second blocking member blocks the at least one water jet from the water injection means, and a fourth position or an open position where the second blocking member does not block the at least one water jet from the water injection means. The second axis may be parallel to the first axis along which the first blocking member moves back and forth. The second blocking member may be positioned between the first blocking member and the support member, or between the water injection means and the first blocking member. In one example, referring to FIGS. 5A-5C, the second blocking member 60 comprising at least one aperture 62 and a non-apertured area 64 is positioned between the first blocking member 50 and the support member 40, and movable back and forth along a second axis between a third position where the second blocking member 60 blocks at least one water jet 36a from a water injection means 32, and a fourth position where the second blocking member 60 does not block the at least one water jet 36a from the water injection means 32 while the first blocking member 50 is in a second position.

An aperture in a blocking member, the first blocking member if it comprises an aperture and/or the second blocking member, means an aperture through which at least one water jet from the water injection means can pass when the blocking member is in an open position. Therefore, when the blocking member has a void inner space, one aperture may intend to mean a pair of apertures through which at least one water jet from the water injection means can pass through when the blocking member is in the open position.

The aperture in a second blocking member may be in any shape, for example, preferably, a circular shape, a semicircular shape, an elliptical shape, a polygonal shape such as a triangular shape or a quadrilateral shape, a star polygon, a cross shape, and a slit shape such as a straight line shape or a curved line shape. The aperture in the second blocking member may have a width of about 2 mm or more, or about 3 to 50 mm, or about 5 to 30 mm. When the blocking member have a plurality of apertures, the interval between adjacent apertures in the blocking member may be about 2 mm or more, or about 3 to 50 mm, or about 5 to 30 mm. Descriptions of apertures with respect to the aperture in a second blocking member are also applied to optional aperture(s) in a first blocking member.

The first blocking member and/or the second blocking member can be made of, for example, synthetic resin, metal, or the like. In addition, the shape may be appropriately selected as a plate, a roll or the like suitable for a hydroentanglement process of the present invention.

A distance between the water injection means and a blocking member closest to the water injection means may be about 1 mm or about 2 mm, or more, and is adjustable considering equipment design, space between a water injection means and a support. When the distance between the blocking member and the water injection means is less than 1 mm, the blocking member and the water injection means may be in contact with each other, and one or both of them are damaged. A distance between the blocking member (the blocking member located in the highest position when the apparatus has more than one blocking member) and the orifice may be about 30 mm or less. A distance between the fibrous web and the blocking member closest to the fibrous web may be about 5 mm to 50 mm. When the distance between the blocking member and the fibrous web may be less than 5 mm, the fibrous web may be damaged by the contact between the blocking member and the fibrous web. When the distance between the blocking member and the orifice may be more than 30 mm or the distance between the blocking member and the fibrous web exceeds 50 mm, the energy of the water flow may be reduced and the entanglement may become insufficient.

Support may be in the form of a moving wire screen, rotating porous drum, or the like known in the art suitable for a hydroentanglement process. The support may have a patterned surface exhibiting depressions, apertures, and/or projections. The fibrous web receives its image or decoration against the wire gauze, plate or drum by being formed respectively against depression, apertures and/or projections with the help of water jets.

Nonwoven

A nonwoven which can be produced by the process of the present invention described in detail herein has a length and a width, and comprises a plurality of first areas comprising hydroentangled fibers and at least one second area located between two adjacent first areas in a nonwoven lengthwise direction, so that the plurality of first areas are discrete in the nonwoven lengthwise direction. The nonwoven lengthwise direction corresponds to a machine direction in a nonwoven making process.

Each of the first areas comprises at least two apertures or depressions, and a land between the two apertures or the two depressions. The land in the first area has a higher fiber density or a higher degree of fiber entanglement than the second area as the first area went through additional hydroentanglement process. The land in the first area may have a thickness in a z-direction lower than the second area as the first area went through additional hydroentanglement process.

The second area may be in the state of any of fiber assemblies, such as the state of unbonded web, the state of bonded web, the state of entangled web, and the like, and are not particularly limited. In some embodiments, the second area comprises entangled fiber. The entanglement of fibers in the second area can be carried out by any method such as a needle punching method, a hydro-entangling method, a water vapor flow (steam jetting) entangling method, and the like. Since the formation of the plurality of first areas is carried out by a hydroentangling method, it may be preferable to carry out the entanglement of fibers in the second area by a hydroentangling method. In other embodiments, the second area comprises thermal-fused fibers.

The nonwoven of the present invention provides a cushiony and soft sensory as well as a pattern as the second area maintains an original caliper during the hydroentanglement process.

The plurality of first areas may comprise a pattern. Each of the first areas may have a shape of a linear line, a curved line, a circle, an ellipse, a triangle, a polygon, a chevron pattern, a lattice pattern, a sawtooth pattern, a zigzag pattern, and the like. In some embodiments, the plurality of first areas comprise a repeated pattern at least in a nonwoven lengthwise direction. Each of the plurality of first areas are not necessarily in the same shape or size.

Figure 6:
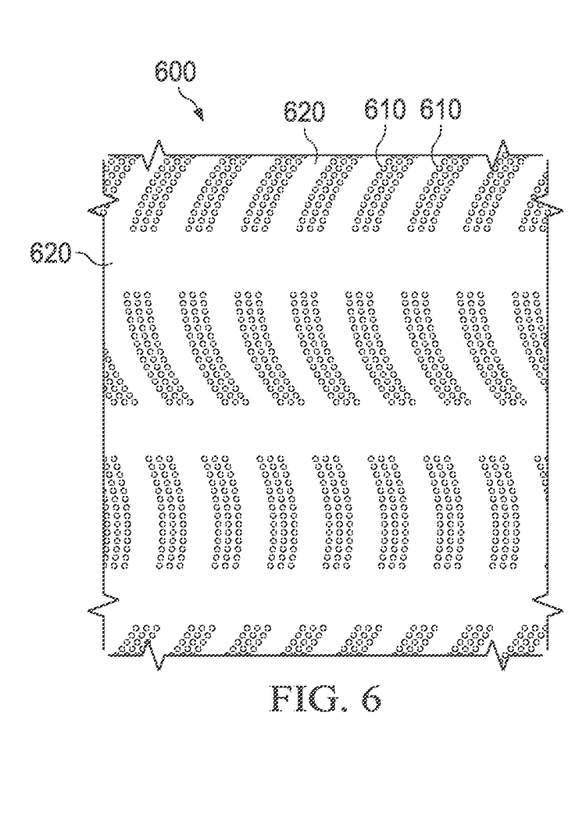
FIG. 6 is a plan view of a nonwoven according to the present invention.

In some embodiments, the plurality of first areas are continuous in a nonwoven widthwise direction which corresponds to a cross-machine direction. In other embodiments, the plurality of first areas are discrete in a nonwoven widthwise direction so that the plurality of first areas is surrounded by the second area. Referring to FIG. 6, in an embodiment, a hydroentangled nonwoven 600 of the present invention has a plurality of first areas 610 discrete in a nonwoven widthwise direction and a second area 620 surrounding the plurality of first areas 610.

Figure 7:
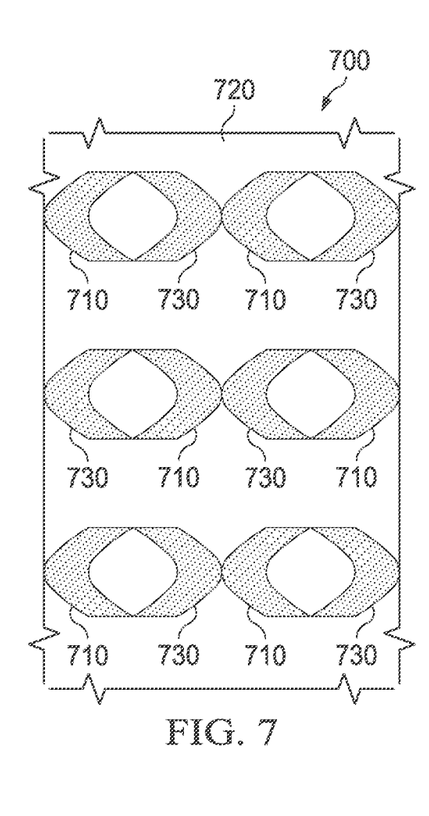
FIG. 7 is a plan view of another nonwoven according to the present invention.

The nonwoven web of the present invention may further comprise a plurality of third areas comprising hydroentangled fibers. The plurality of third areas may be formed simultaneously when the plurality of first areas are formed. The plurality of third areas may be formed prior to or after forming the plurality of first areas. The plurality of third areas may also be formed in such a manner as to intersect a portion of the plurality of first areas, may also be formed between adjacent a plurality of first areas, and may also be formed inside the plurality of first areas. The plurality of third areas may have the same shape as the first areas. The third areas may have a different shape from the first areas. The third areas may be continuous in a nonwoven lengthwise direction. The third areas may be discrete in a nonwoven lengthwise direction. Referring to FIG. 7, in an embodiment, a hydroentangled nonwoven 700 of the present invention has a plurality of third areas 730 as well as a plurality of first areas 710 discrete in a nonwoven widthwise direction and at least one second area 720 between two adjacent first areas 710 in a nonwoven lengthwise direction.

Included in the hydroentangled nonwoven can be fibers of natural or man-made origin and may be staple fibers or continuous filaments or be formed in situ. The fibers can be a cellulosic fibrous component, a non-cellulosic fibrous component, a polyolefin-based binder fibrous component, and any combination thereof. The polyolefin-based binder fibrous component can be a bicomponent fiber. As used hereinafter the term bicomponent fibers refers to fibers having two constituents.

The nonwoven of the present invention can be manufactured from an assortment of suitable fiber types that produce the desired softness, mechanical performance and fluid handling performance considering final use of the nonwoven.

The nonwoven web of the present invention may have a basis weight of about 200 grams per square meter (gsm) or less, of bout 25-100 gsm, or of 30-60 gsm.

Laminate

The present invention also provides a laminate comprising a first layer comprising a nonwoven according to the present invention. The laminate of the present invention may further comprise a second layer comprising a nonwoven web or film.

The nonwoven or the laminate according to the present invention can be incorporated into, for example, an absorbent article. For example, it can be used as a component such as a topsheet for a sanitary napkin or a diaper.

Absorbent Article

The present invention also provides an absorbent article comprising a layer comprising a nonwoven or a laminate according to the present invention.

The absorbent article of the present invention may comprise a topsheet and a backsheet joined to the topsheet. The absorbent article of the present invention may further comprise an absorbent core disposed between the topsheet and the backsheet. In some embodiments, the absorbent article of the present invention comprises a topsheet or a layer disposed below the topsheet comprising a nonwoven or a laminate according to the present invention.

The absorbent articles of the present invention may be produced industrially by any suitable means. The different layers may thus be assembled using standard means such as embossing, thermal bonding, gluing or any combination thereof.

Topsheet

Topsheet can catch body fluids and/or allow the fluid penetration inside the absorbent article. With the nonwoven according to the present invention, the first web layer is preferably, disposed on a side in contact with the skin.

Backsheet

Any conventional liquid impervious backsheet materials commonly used for absorbent articles may be used as backsheet. In some embodiments, the backsheet may be impervious to malodorous gases generated by absorbed bodily discharges, so that the malodors do not escape. The backsheet may or may not be breathable.

Absorbent Core

It may be desirable that the absorbent article further comprises an absorbent core disposed between the topsheet and the backsheet. As used herein, the term "absorbent core" refers to a material or combination of materials suitable for absorbing, distributing, and storing fluids such as urine, blood, menses, and other body exudates. Any conventional materials for absorbent core suitable for absorbent articles may be used as absorbent core.

EXAMPLES

Example 1: Preparation of Nonwoven

Rayon fibers (1.7 Dtex, 57 mm length, Lenzing, China) and PE/PET sheath/core bicomponent fibers (2.2 Dtex, 57 mm length, JNC, Japan) are mixed with a ratio of 80 wt % to 20 wt % and form a fibrous web with a basis weight of 40 gsm through a carding process. The fibrous web moves at a speed of 50 meter/min to a first hydroentanglement system having two injectors. Water jets from a first injector are applies at 3.0 MPa to the fibrous web, and then water jets from a second injector are applied at 2.5 MPa to the opposite side of the fibrous web to further entangle fibers in the fibrous web.

Then the fibrous web is moved to a second hydroentanglement system similar to one shown in FIGS. 5A-5C. Referring to FIG. 5A, water jets 36 from an injector 32 of the second hydroentanglement system are applied at 5.0 MPa to the fibrous web 30. The second hydroentanglement system has a first blocking member 50, a blocker plate in this case, disposed between the injector 32 and the fibrous web 30, and a second blocking member 60, an apertured plate in this case, disposed between the blocker plate 60 and the fibrous web 30.

The apertured plate 60 has apertures 62 with 2 mm of diameter spaced away a 2 mm from an adjacent aperture, and moves back and forth in a cross-machine direction with a 15 mm range and a frequency of 20 rounds/sec between a first position, a blocking position, where at least one water jet 36a from the injector 32 is blocked by the apertured plate 60, and a second position, an open position, where the at least one water jet 36a from the injector 32 passes through an aperture 62 of the apertured plate 60. The distance between the apertured plate 60 and the fibrous web 30 is about 10 mm. The blocker plate 50 moves in a machine direction to block the aperture 62 in the apertured plate 60 for about 0.12 sec at frequency of 40 rounds/secs. A hydroentangled nonwoven 600 shown in FIG. 6 having a plurality of first areas 610 discrete in a machine direction and a second area 620 is produced. The obtained nonwoven goes through a dryer to dry the nonwoven.

Example 2: Preparation of Nonwoven

A hydroentangled nonwoven is produced according to the process disclosed in Example 1. Bleached cotton fibers (1.7 Dtex, 57 mm length, Marusan Co., LTD, CN) and PE/PET sheath/core bicomponent fibers (2.2 Dtex, 57 mm length, JNC, Japan) are mixed with a ratio of 80 wt % to 20 wt % and from a fibrous web. The fibrous web moves at a speed of 50 meter/min to a first hydroentanglement system having two injectors and is hydroentangled under the conditions disclosed in Example 1. Then the fibrous web is moved to a second hydroentanglement system as disclosed in Example 1. The second hydroentanglement system has an apertured hollow cylinder having a diameter of 3 inches, and rotating along the axis X in a speed of 1.73 rounds/sec (50 meter/min). A distance between two adjacent apertures is about 60 mm in a cross-machine direction, and about 80 mm in a machine direction. The obtained nonwoven goes through a dryer to dry the nonwoven.

Figure 8:
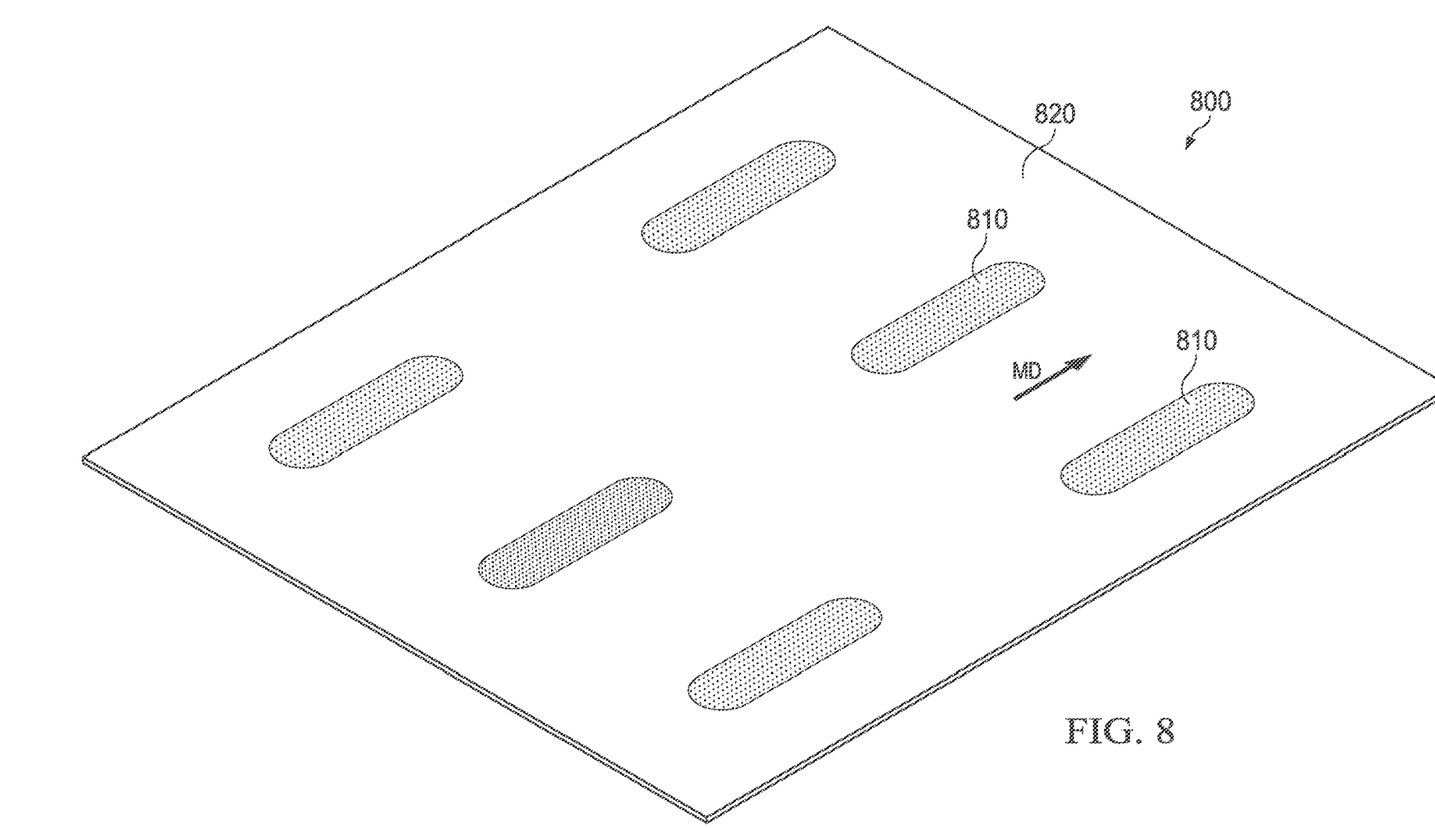
FIG. 8 is a plan view of another nonwoven according to the present invention.
Figure 9:
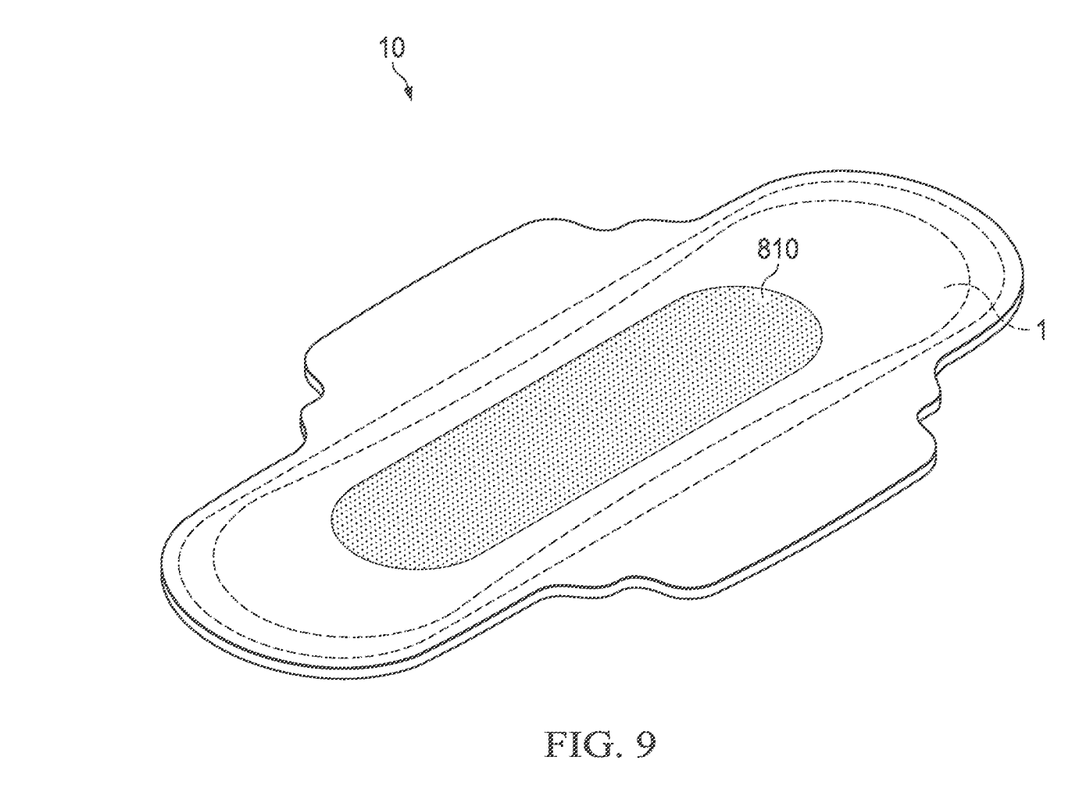
FIG. 9 is a perspective view of one example of an absorbent article that incorporates a nonwoven according to the present invention.

The obtained hydroentangled nonwoven 800 shown in FIG. 8 has a plurality of first areas 810 discrete in a machine direction and a second area 820. The nonwoven 800 can be used as a topsheet 1 of a sanitary napkin 10 as shown in FIG. 9 in such a way that the first area 810, an apertured pattern, is positioned in a center area of the sanitary napkin 10.

This application claims the benefit of Application No. CN2018/088351, filed on May 25, 2018, the entirety of which is incorporated by reference herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for making a nonwoven comprising a plurality of first areas comprising hydroentangled fibers, the process comprising:
    subjecting a fibrous web to a first hydroentanglement process directing water jets from a water injection means comprising a plurality of orifices on to the fibrous web, and
    blocking at least one water jet from the water injection means discontinuously by use of a first blocking member positioned between the water injection means and the fibrous web, wherein the first blocking member moves back and forth along a first axis between a first position where the first blocking member blocks the at least one water jet and a second position where the first blocking member does not block the at least one water jet; and
    blocking the at least one water jet not blocked by the first blocking member by use of a second blocking member comprising at least one aperture, wherein the second blocking member moves back and forth along a second axis, not parallel to the first axis, between a third position where the second blocking member blocks the at least one water jet not blocked by the first blocking member and a fourth position where the second blocking member does not block the at least one water jet not blocked by the first blocking member, wherein the first areas comprising hydroentangled fibers are discrete in a machine direction.

2. The process according to claim 1, wherein the first axis is parallel to the machine direction.

3. The process according to claim 1, wherein the second blocking member is positioned either between the water injection means and the first blocking member, or between the first blocking member and the fibrous web.

4. The process according to claim 1, wherein the fibrous web subjected to the first hydroentanglement process is an entangled web or a thermal bonded web.

5. The process according to claim 1, wherein the process further comprises subjecting the fibrous web to an entanglement process prior to the first hydroentanglement process.

6. The process according to claim 1, wherein the process further comprises subjecting the fibrous web to an entanglement process after the first hydroentanglement process.

7. The process according to claim 1, wherein the first blocking member comprises at least one aperture.

8. The process according to claim 1, wherein the at least one water jet from the water injection means is discontinuously blocked in a constant speed.

9. The process according to claim 1, wherein the at least one water jet from the water injection means is discontinuously blocked in a non-constant speed.

10. The process according to claim 1, wherein the first areas comprising hydroentangled fibers are discrete in a cross-machine direction.

11. The process according to claim 1, wherein each of the first areas comprising hydroentangled fibers comprises at least two apertures, and a land between the two apertures.

* * * * *